United States Patent
Reddy et al.

(10) Patent No.: US 7,230,006 B2
(45) Date of Patent: Jun. 12, 2007

(54) CRYSTALLINE FORM III OF ANHYDROUS MOXIFLOXACIN HYDROCHLORIDE AND A PROCESS FOR PREPARATION THEREOF

(75) Inventors: Manne Satyanarayana Reddy, Hyderabad (IN); Sajja Eswaraiah, Hyderabad (IN); Vetukuri Venkata Naga Kali Vara Prasada Raju, Hyderabad (IN); Rapolu Rajesh Kumar, Nalgonda (IN); Ningam Srinivasreddy, Zahirabad (IN); Vedantham Ravindra, Guntur (IN)

(73) Assignees: Reddy's Laboratories Limited, Hyderabad (IN); Reddy's Laboratories, Inc., Upper Saddle River, NJ (US)

( * ) Notice: Subject to any disclaimer, the term of this patent is extended or adjusted under 35 U.S.C. 154(b) by 233 days.

(21) Appl. No.: 10/822,154

(22) Filed: Apr. 9, 2004

(65) Prior Publication Data

US 2005/0137227 A1 Jun. 23, 2005

(30) Foreign Application Priority Data

Sep. 4, 2003 (IN) .................. 308/MAS/2003

(51) Int. Cl.
*C07D 471/02* (2006.01)
*A61K 31/44* (2006.01)

(52) U.S. Cl. ..................................... 514/300; 546/113

(58) Field of Classification Search ................ 514/300; 546/113

See application file for complete search history.

(56) References Cited

U.S. PATENT DOCUMENTS 5,849,752 A * 12/1998 Grunenberg et al. ........ 514/300

* cited by examiner

*Primary Examiner*—D. Margaret Seaman
(74) *Attorney, Agent, or Firm*—Robert A. Franks; Milagros A. Cepeda

(57) ABSTRACT

A new crystalline Form III of moxifloxacin monohydrochloride and processes for making the crystalline form as well as compositions, pharmaceutical compositions, and methods utilizing the crystalline form are described.

26 Claims, 5 Drawing Sheets

Thermal Analysis Data

CRYSTALLINE FORM III OF ANHYDROUS MOXIFLOXACIN HYDROCHLORIDE AND A PROCESS FOR PREPARATION THEREOF

CROSS-REFERENCE TO RELATED APPLICATION

This application claims priority of Indian Patent Application No. 308/MAS/2003, filed Apr. 9, 2003, of which entire content is incorporated herein by reference.

BACKGROUND OF THE INVENTION

Moxifloxacin monohydrochloride is a synthetic broad-spectrum antibacterial agent. The active moiety, moxifloxacin has been shown to be clinically active against most strains of microorganisms such as aerobic gram-positive microorganisms including *staphylococcus aureus* (methicillin-susceptible strains only), *streptococcus pneumoniae* (penicillin-susceptible strains), and *streptococcus pyogenes*; aerobic gram-negative microorganisms including *haemophilus influenzae, haemophilus parainfluenzae, klebisiella pneumoniae,* and *moraxella catarrhalis*; and other microorganisms like *chlamydia pneumoniae* and *mycoplasma pneumoniae*.

SUMMARY OF INVENTION

In accordance with one aspect, the invention provides a novel crystalline Form III of anhydrous moxifloxacin monohydrochloride. The crystalline Form III of moxifloxacin monohydrochloride may be characterized by an X-ray diffraction pattern, expressed in terms of 2θ angles and obtained with a diffractometer equipped with a copper K X-radiation source, wherein the X-ray powder diffraction pattern includes five or more peaks selected from the group consisting of peaks with 2 theta angles of 5.6±0.09, 7.1±0.09, 8.4±0.09, 8.8±0.09, 10.0±0.09, 10.4±0.09, 10.4±0.09, 11.4±0.09, 12.2±0.09, 13.1±0.09, 13.9±0.09, 14.4±0.09, 14.7±0.09, 16.6±0.09, 16.9±0.09, 17.2±0.09, 17.7±0.09, 18.5±0.09, 19.1±0.09, 19.2±0.09, 19.8±0.09, 20.1±0.09, 20.3±0.09, 21.1±0.09, 21.5±0.09, 22.1±0.09, 22.6±0.09, 22.9±0.09, 23.5±0.09, 24.0±0.09, 24.6±0.09, 24.9±0.09, 25.8±0.09, 26.2±0.09, 26.6±0.09, 26.9±0.09, 27.2±0.09, 28.7±0.09, 29.1±0.09, 29.7±0.09, 30.1±0.09, 31.4±0.09, 32.1±0.09, 37.3±0.09, 39.0±0.09, 40.8±0.09, 41.5±0.09, 42.2±0.09, and 43.1±0.09 degrees. The crystalline Form III of moxifloxacin monohydrochloride may also be characterized by an X-ray diffraction pattern, expressed in terms of 2θ angles and obtained with a diffractometer equipped with a copper K X-radiation source, wherein the X-ray powder diffraction pattern includes two or more peaks selected from the group consisting of peaks with 2 theta angles of 7.1±0.09, 8.8±0.09, 13.1±0.09, 13.9±0.09, 16.6±0.09, 17.7±0.09, and 22.1±0.09. The crystalline form III of anhydrous moxifloxacin monohydrochloride may also be characterized by other analytical methods. Various other embodiments and variants are also provided.

In another aspect, the invention provides a composition that includes moxifloxacin in a solid form, wherein at least 80% by weight of the solid moxifloxacin monohydrochloride is the crystalline form III of anhydrous moxifloxacin monohydrochloride. The crystalline form III of anhydrous moxifloxacin monohydrochloride in the composition of this aspect of the invention may be characterized by the XRD patterns as described.

The invention also relates to a process for preparing the crystalline form III of moxifloxacin monohydrochloride and to a pharmaceutical composition that includes the crystalline form III of moxifloxacin monohydrochloride and one or more pharmaceutically acceptable carriers or diluents. The pharmaceutical composition may also include one or more additional active ingredients. Preferably, the pharmaceutical composition is in a solid dosage form for oral administration, such as a tablet.

The invention also relates to a method of preventing or treating allergic syndromes, by administering to a patient in need of such treatment an effective amount of crystalline form III of anhydrous moxifloxacin monohydrochloride.

DESCRIPTION OF THE ACCOMPANYING DRAWINGS

DETAILED DESCRIPTION OF THE INVENTION

Figure 1:
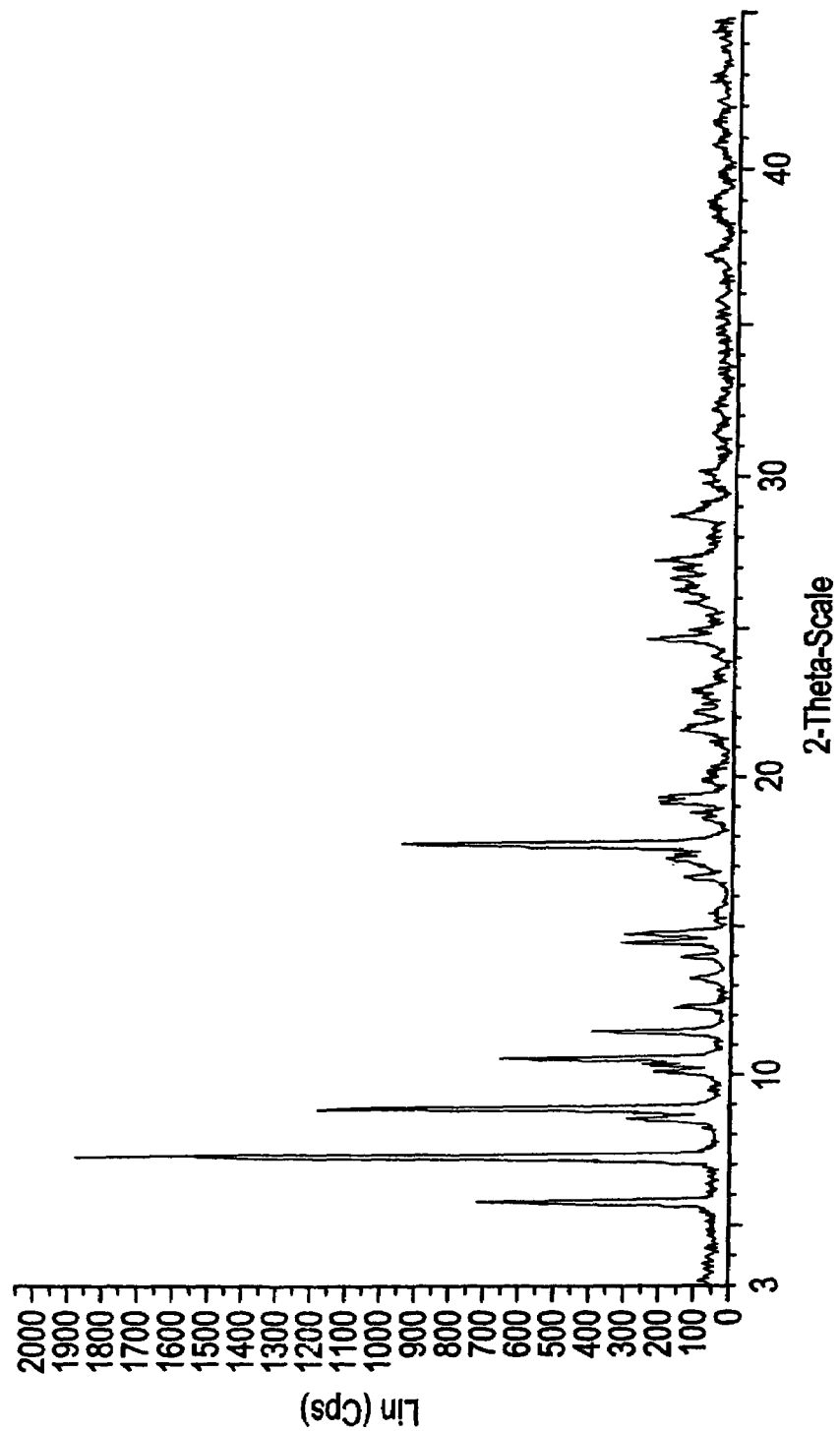
FIG. 1 is a sample of X-ray powder diffractogram of the crystalline form III of moxifloxacin monohydrochloride.

Unless defined otherwise, technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described.

Unless stated to the contrary, any use of the words such as "including," "containing," "comprising," "having" and the like, means "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

For purposes of the present invention, the following terms are defined below.

A "compound" is a chemical substance that includes molecules of the same chemical structure.

"Pharmaceutically acceptable" means that which is useful in preparing a pharmaceutical composition that is generally non-toxic and is not biologically undesirable and includes that which is acceptable for veterinary use and/or human pharmaceutical use.

The term "composition" includes, but is not limited to, a powder, a suspension, an emulsion and/or mixtures thereof. The term composition is intended to encompass a product containing the specified ingredients in the specified amounts, as well as any product, which results, directly or indirectly, from combination of the specified ingredients in the specified amounts. A "composition" may contain a single compound or a mixture of compounds.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the active ingredient, additional active ingredient(s), and pharmaceutically acceptable excipients.

The term "excipient" means a component of a pharmaceutical product that is not the active ingredient, such as filler, diluent, carrier, and so on. The excipients that are useful in preparing a pharmaceutical composition are preferably generally safe, non-toxic and neither biologically nor otherwise undesirable, and are acceptable for veterinary use as well as human pharmaceutical use. "A pharmaceutically acceptable excipient" as used in the specification and claims includes both one and more than one such excipient.

The term "isolating" is used to indicate separation of the compound being isolated regardless of the purity of the isolated compound from any unwanted substance which presents with the compound as a mixture. Thus, degree of the purity of the isolated or separated compound does not affect the status of "isolating".

The term "lower alkyl alcohol" as used in the claims defines alcohols having from 1 to 8 carbon atoms and capable of dissolving moxifloxacin monohydrochloride or moxifloxacin at their reflux temperatures with solubility of at least 0.05 g/ml (drug-to-solvent).

The term "substantially free of" in reference to a composition, as used herein, means that the substance cannot be detected in the composition by methods known to those skilled in the art at the time of the filing of this application.

The term "crystalline Form III of anhydrous moxifloxacin monohydrochloride" is used to refer to a new polymorphic form of anhydrous moxifloxacin monohydrochloride obtained by the inventors. In the Indian Patent Application No. 308/MAS/2003, the benefit of priority of which is sought for the present patent application, the substance defined herein as crystalline Form III of anhydrous moxifloxacin monohydrochloride is referred to as "crystalline Form II." The invention contemplates the actual substance of the crystalline Form III of anhydrous moxifloxacin monohydrochloride regardless of its particle size, method of preparation and/or methods of analytical characterization.

Moxifloxacin monohydrochloride is 1-cyclopropyl-7-([S,S]-2,8-diazabicyclo-[4.3.0]non-8-yl)-6-fluoro-1,4-dihydro-8-methoxy-4-oxo-3-quinoline carboxylic acid mono hydrochloride, which is a hydrochloric acid salt of 1-cyclopropyl-7-([S,S]-2,8-diazabicyclo-[4.3.0]non-8-yl)-6-fluoro-1,4-dihydro-8-methoxy-4-oxo-3-quinoline carboxylic acid in 1:1 molar ratio, and has the structure as follows:

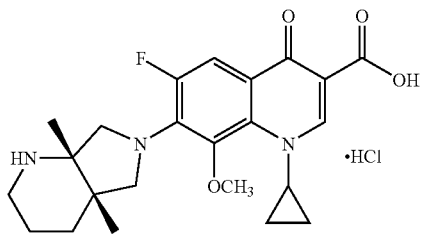

As a molecule, moxifloxacin monohydrochloride is described in U.S. Pat. No. 5,607,942, of which entire content is incorporated by reference herein. However, it is known that polymorphic forms of the same drug may have substantial differences in certain pharmaceutically important properties such as dissolution characteristics and bioavailability as well as stability of the drug. Furthermore, difference crystalline form may have different particle size, hardness and glass transition temperature. Thus, one crystalline form may provide significant advantages over other crystalline forms of the same drug in solid dosage form manufacture process such as accurate measurement of the active ingredients, easier filtration, or improved stability during granulation or storage. Furthermore, a particular process suitable for one crystalline form may also provide drug manufacturers several advantages such as economically or environmentally suitable solvents or process, or higher purity or yield of the desired product.

U.S. Pat. No. 5,849,752 ("the '752 patent"), incorporated by reference, discloses certain specific crystalline forms of anhydrous moxifloxacin monohydrochloride and monohydrated moxifloxacin monohydrochloride. For convenience, the anhydrous crystalline form disclosed in the '752 patent is designated as "Form I," and the hydrated form as "Form II." The '752 patent discloses X-ray diffraction patterns of the form I and II as shown in the following table 1:

TABLE 1

| X-ray diffraction patterns (2 θ) | |
|---|---|
| Anhydrous form I | Hydrated form II |
| 5.8 | 5.8 |
| 8.6 | 8.5 |
| 10.3 | 10.1 |
| 11.6 | 11.6 |
| 13.6 | 13.4 |
| 14.5 | 14.5 |
| 15.0 | 14.8 |
| 15.8 | 15.6 |
| 17.3 | 17.0 |
| 17.5 | 17.2 |
| 18.3 | 17.4 |
| 18.9 | 17.5 |
| 19.3 | 17.9 |
| 19.6 | 18.6 |
| 20.6 | 19.1 |
| 21.5 | 19.6 |
| 22.5 | 20.4 |
| 22.8 | 21.1 |
| 23.0 | 21.8 |
| 23.8 | 22.7 |
| 24.2 | 23.0 |
| 24.7 | 23.6 |
| 25.0 | 24.1 |
| 26.3 | 24.5 |
| 27.0 | 26.5 |
| 27.4 | 26.7 |
| 27.8 | 27.0 |

TABLE 1-continued

X-ray diffraction patterns (2 θ)

| Anhydrous form I | Hydrated form II |
|---|---|
| 28.2 | 27.3 |
| 29.4 | 27.5 |
| 29.7 | 27.8 |
| 30.0 | 28.5 |
| 30.3 | 28.9 |
| 31.3 | 29.2 |
| 31.8 | 29.7 |
| 34.5 | 31.4 |
| 35.3 | 31.9 |
| 37.1 | 32.3 |
|  | 32.6 |
|  | 34.2 |
|  | 35.1 |
|  | 35.5 |
|  | 36.8 |
|  | 37.5 |

Other spectra such $^{13}$C solid state NMR, IR, DSC, thermogravimetry and Raman of the form I and II are also disclosed in the '752 patent.

According to one aspect, the present invention provides a new crystalline Form III of anhydrous moxifloxacin monohydrochloride, which is different from the Form I and Form II of the '752 patent. The crystalline Form III of anhydrous moxifloxacin monohydrochloride may be prepared by a process including refluxing azeotropically a mixture of moxifloxacin monohydrochloride and a solvent selected from the group consisting of lower branched or chained acid esters, aliphatic ketones and aliphatic hydrocarbon solvents to form a mixture; cooling the refluxed mixture until solids separate; and isolating said solids thereby obtaining said crystalline form III of moxifloxacin monohydrochloride. Non-limiting examples of the suitable solvents include tertiary butyl acetate, cyclohexane, and toluene. Alternatively, the crystalline Form III of anhydrous moxifloxacin monohydrochloride may be prepared by a process including dissolving moxifloxacin hydrochloride in a lower alkyl alcohol to obtain a solution; adding to the solution an anti solvent, in which moxifloxacin hydrochloride is poorly soluble but which is miscible with said lower alkyl alcohol; cooling the resulted mixture after adding the anti solvent until solids separate; and isolating said solids thus obtaining the crystalline form III of moxifloxacin monohydrochloride. Preferably, the suitable lower alkyl alcohols with moxifloxacin or moxifloxacin monohydrochloride solubility greater than 0.075 g/ml are used; more preferred lower alkyl alcohols have solubility greater than 0.1 g/ml on drug to solvent basis. The suitable lower alkyl alcohols include, for example, methanol, ethanol, t-butyl alcohol, isopropyl alcohol, other commonly used alkyl alcohol solvents, and mixtures thereof. A suitable non-limiting example of the anti solvent is acetonitrile.

The cooling step of the both processes may be accompanied by stirring the mixtures. The isolation of the solids can be easily done by conventional methods such as filtration, and the isolated compound may be dried at an elevated temperature, which is preferably at about 30–100° C., more preferably at about 60–90° C.

In one particular embodiment of the process aspect of the invention, the preparation of the crystalline Form III of anhydrous moxifloxacin hydrochloride includes:

i) refluxing azeotropically the starting moxifloxacin hydrochloride in lower branched or chained acid esters such as tertiary butyl acetate or an aliphatic hydrocarbon solvent such as cyclohexane or aromatic hydrocarbons such as toluene;
ii) cooling the reaction mixture of step (i) accompanied by stirring of the mixture till the solid mass crystallizes;
iii) isolating the solid obtained in step (ii) by conventional methods;
iv) drying the isolated compound of step (iii) with or without vacuum at 30–100° C., preferably 60–90° C. to afford the crystalline Form III of anhydrous moxifloxacin hydrochloride.

In another particular embodiment of the process aspect of the invention, the preparation of the crystalline Form III of anhydrous moxifloxacin hydrochloride includes:

i) dissolution of the starting moxifloxacin hydrochloride in $C_1$–$C_6$ alcohols, such as methanol, at 25–70° C., preferably at 60–65° C.;
ii) adding an anti solvents, such as acetonitrile, in which the product is poorly soluble;
iii) cooling the solution mixture of step (ii) accompanied by stirring of the mixture till the solid mass crystallizes;
iv) isolating the solid obtained in step (iii) by conventional methods;
v) drying the isolated compound of step (iv) with or without vacuum at 30–100° C., preferably 60–90° C. to afford the crystalline Form III of anhydrous moxifloxacin hydrochloride.

The crystalline form III of moxifloxacin monohydrochloride produced by the inventors was characterized by an X-ray powder diffraction pattern. An example of one X-ray diffraction analysis is shown in FIG. 1, and the characteristic 2 theta values (in degrees) in the X-ray diffractograms are shown in Table 2:

TABLE 2

| 2 theta (°) |
|---|
| 5.6 |
| 7.1 |
| 8.4 |
| 8.8 |
| 10.0 |
| 10.4 |
| 11.4 |
| 12.2 |
| 13.1 |
| 13.9 |
| 14.4 |
| 14.7 |
| 16.6 |
| 16.9 |
| 17.2 |
| 17.7 |
| 18.5 |
| 19.1 |
| 19.2 |
| 19.8 |
| 20.1 |
| 20.3 |
| 21.1 |
| 21.5 |
| 22.1 |
| 22.6 |
| 22.9 |
| 23.5 |
| 24.0 |
| 24.6 |
| 24.9 |
| 25.8 |
| 26.2 |
| 26.6 |
| 26.9 |

TABLE 2-continued

| 2 theta (°) |
| --- |
| 27.2 |
| 28.7 |
| 29.1 |
| 29.7 |
| 30.1 |
| 31.4 |
| 32.1 |
| 37.3 |
| 39.0 |
| 40.8 |
| 41.5 |
| 42.2 |
| 43.1 |

The X-ray diffractogram was measured on a Bruker Axs, D8 Advance Powder X-ray Diffractometer with Cu K alpha-1 radiation source.

It should be kept in mind that slight variations in the observed 2 theta angles values are expected based on the specific diffractometer employed, the analyst and the sample preparation technique. More variation is expected for the relative peak intensities, which is largely affected by the particle size of the sample. Thus, identification of the exact crystalline form of a compound should be based primarily on observed 2 theta angles with lesser importance attributed to relative peak intensities. The 2 theta diffraction angles and corresponding d-spacing values account for positions of various peaks in the X-ray powder diffraction pattern. D-spacing values are calculated with observed 2 theta angles and copper K($\alpha$1) wavelength using the Bragg equation well known to those of skill in the art. Table 3 shows the results of another X-ray diffraction analysis of a sample of crystalline Form III of anhydrous moxifloxacin monohydrochloride, demonstrating the variability in the observed 2 theta angles values:

TABLE 3

| 2 theta (°) |
| --- |
| 5.7 |
| 7.1 |
| 8.5 |
| 8.8 |
| 10.0 |
| 10.2 |
| 10.5 |
| 11.4 |
| 12.2 |
| 13.1 |
| 14.0 |
| 14.4 |
| 14.7 |
| 15.1 |
| 15.5 |
| 16.5 |
| 17.2 |
| 17.7 |
| 18.5 |
| 19.2 |
| 19.7 |
| 20.3 |
| 21.6 |
| 22.2 |
| 23.0 |
| 23.6 |
| 24.0 |
| 24.6 |
| 25.0 |
| 25.7 |

TABLE 3-continued

| 2 theta (°) |
| --- |
| 26.4 |
| 27.2 |
| 27.8 |
| 28.3 |
| 28.9 |
| 29.9 |
| 32.2 |
| 34.9 |
| 35.9 |
| 36.6 |
| 37.3 |
| 39.0 |
| 41.2 |
| 41.8 |
| 44.6 |

Thus, some margin of error may be present in each of the 2 theta angle assignments reported herein. The assigned margin of error in the 2 theta angles for the crystalline form of moxifloxacin monohydrochloride is approximately ±0.09 for each of the peak assignments. In view of the assigned margin of error, in a preferred variant, the crystalline form III of anhydrous moxifloxacin monohydrochloride may be characterized by an X-ray diffraction pattern, expressed in terms of 2 theta angles, that includes four or more peaks selected from the group consisting of 5.6±0.09, 7.1±0.09, 8.4±0.09, 8.8±0.09, 10.0±0.09, 10.4±0.09, 10.4±0.09, 11.4±0.09, 12.2±0.09, 13.1±0.09, 13.9±0.09, 14.4±0.09, 14.7±0.09, 16.6±0.09, 16.9±0.09, 17.2±0.09, 17.7±0.09, 18.5±0.09, 19.1±0.09, 19.2±0.09, 19.8±0.09, 20.1±0.09, 20.3±0.09, 21.1±0.09, 21.5±0.09, 22.1±0.09, 22.6±0.09, 22.9±±0.09, 23.5±±0.09, 24.0±0.09, 24.6±0.09, 24.9±0.09, 25.8±0.09, 26.2±0.09, 26.6±0.09, 26.9±0.09, 27.2±0.09, 28.7±0.09, 29.1±0.09, 29.7±0.09, 30.1±0.09, 31.4±0.09, 32.1±0.09, 37.3±0.09, 39.0±0.09, 40.8±0.09, 41.5±0.09, 42.2±0.09, and 43.1±0.09 degrees.

Comparing the XRD data in Tables 1, 2, and 3, it is apparent that certain peaks provide the best way of characterizing the crystalline Form III of anhydrous moxifloxacin monohydrochloride and of differentiating it from the Forms I and II. Very few of such peaks are needed to allow for such characterization and differentiation, including presence of the crystalline Form III of anhydrous moxifloxacin monohydrochloride in mixtures with other forms of moxifloxacin. Thus, the crystalline Form III of anhydrous moxifloxacin monohydrochloride may also be characterized by an X-ray powder diffraction pattern includes two or more peaks selected from the group consisting of peaks with 2 theta angles of 7.1±0.09, 8.8±0.09, 13.1±0.09, 13.9±0.09, 16.6±0.09, 17.7 0.09, and 22.1±0.09.

Since some margin of error is possible in the assignment of 2 theta angles and d-spacings, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified crystalline form of moxifloxacin monohydrochloride over FIG. 1 and readily determine whether the X-ray diffraction pattern of the unidentified form is substantially the same as the X-ray powder diffraction pattern of the crystalline form of this invention. If the X-ray powder diffraction pattern is substantially the same as FIG. 1, the previously unknown crystalline form of moxifloxacin monohydrochloride can be readily and accurately identified as the crystalline Form III of this invention.

The crystalline Form III of moxifloxacin monohydrochloride is anhydrous. A sample of the crystalline Form III prepared by the inventors had moisture content less than 0.2% by KF method, which confirmed the anhydrous nature of the compound. while the invention is not limited to any specific theory, it should be understood however that the crystalline form III of moxifloxacin monohydrochloride may contain residual, unbound moisture without losing its anhydrous character and/or its crystalline form III characteristics. It is believed that residual moisture may be present in the form of water molecules in the channel of the crystals, rather than being bound inside the crystal lattice as in hydrated forms. When the anhydrous crystalline form is wet, the entire crystalline lattice may expand due to the space occupied by the water molecules. Then the X-ray powder diffraction pattern of the wet crystalline form may also expand. In such case, the X-ray powder diffraction patterns of two different moisture contended crystalline forms may not be perfectly overlapped. Nevertheless, one of the skill in the art should be able to determine whether they are same crystalline forms or not, by looking at the overall shape of the X-ray powder diffraction pattern optionally with help of other spectroscopy data such as Infrared spectroscopy (IR).

Figure 2:
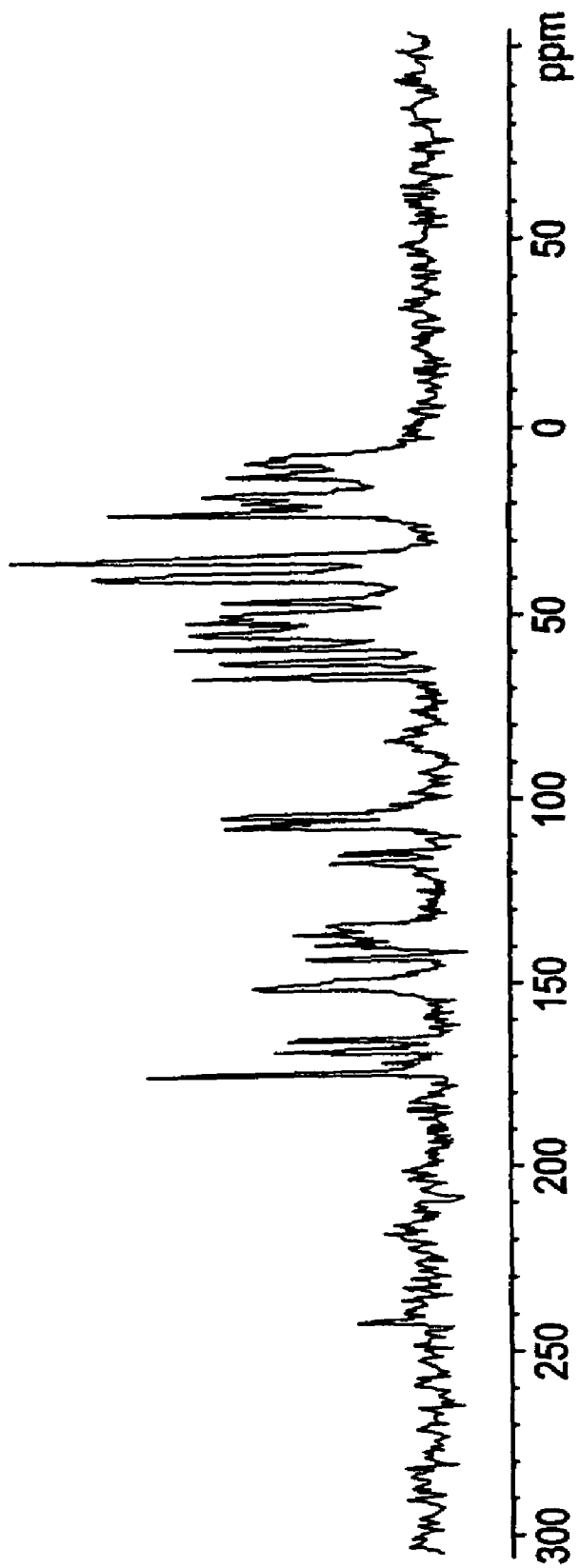
FIG. 2 is a sample of $^{13}$C solid state NMR spectrum of the crystalline form III of moxifloxacin monohydrochloride.
Figure 3:
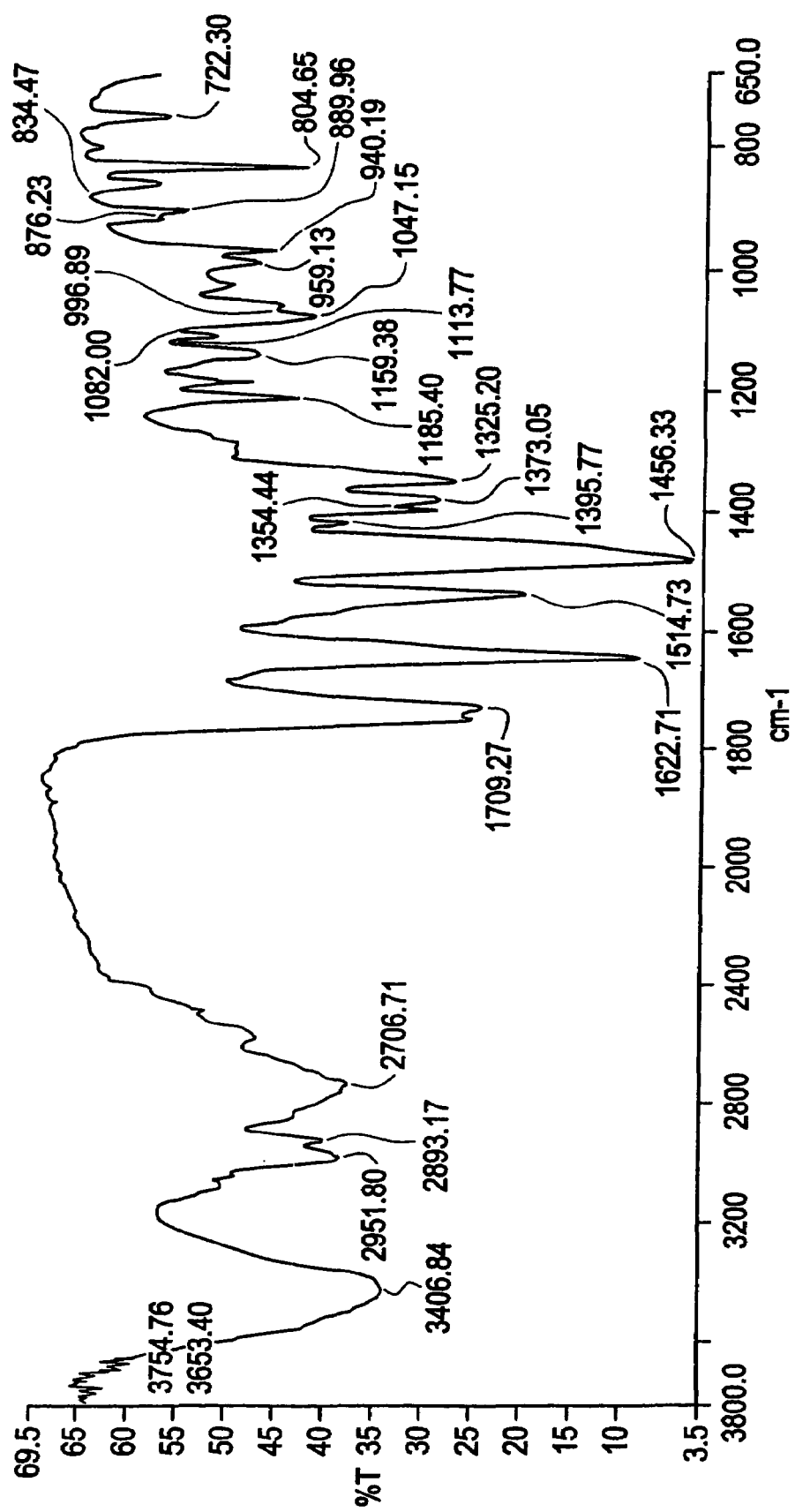
FIG. 3 is a sample of an infrared spectrum of the crystalline form III of moxifloxacin monohydrochloride.
Figure 4:
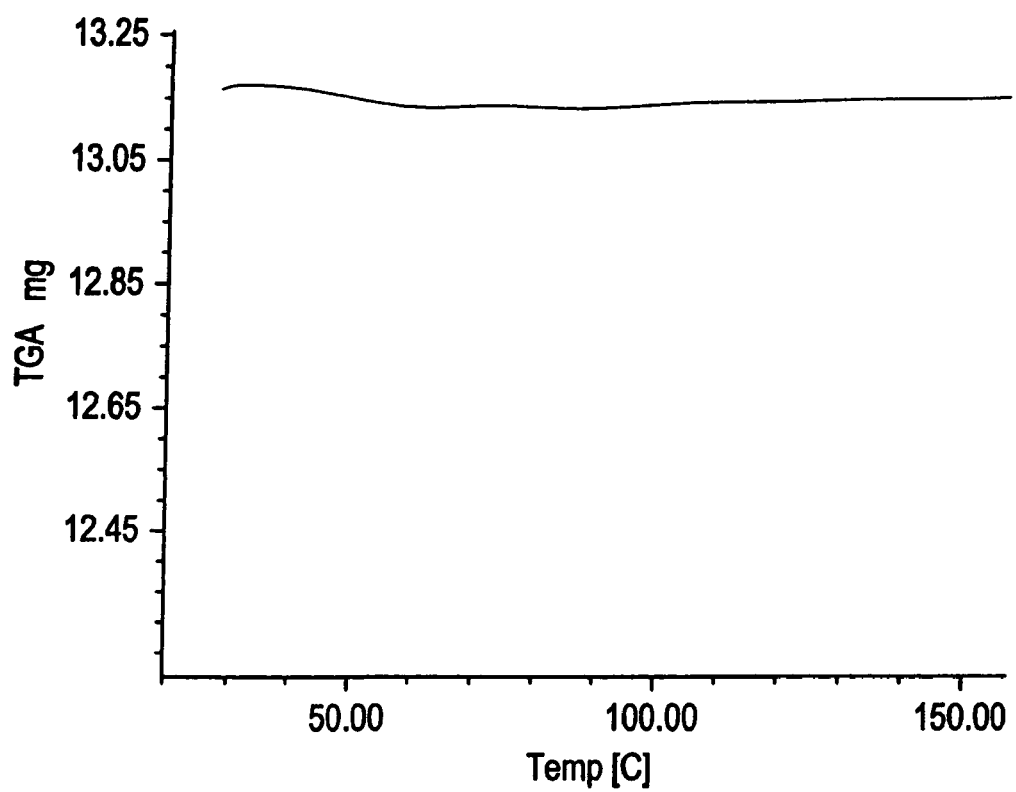
FIG. 4 is a sample of a thermo gravimetric analysis thermogram of the crystalline form III of moxifloxacin monohydrochloride.

The crystalline form III of moxifloxacin monohydrochloride prepared by the inventors was also characterized by $^{13}$C solid state NMR and IR as shown respectively in FIGS. 2 and 3. The NMR spectrum includes a characteristic peak at about 107 ppm. Table 4 shows a comparison between the $^{13}$C solid state NMR spectra of Forms I, II, and III:

TABLE 4

| Form I | Form II | Form III |
|---|---|---|
|  | 7.7 |  |
|  | 8.3 |  |
| 8.5 |  |  |
|  | 9.0 |  |
|  | 10.8 |  |
|  |  | 11.612 |
|  | 12.1 |  |
| 12.3 |  |  |
| 14.1 |  |  |
|  |  | 14.792 |
| 18.2 | 18.2 |  |
|  | 19.8 |  |
| 20.2 |  |  |
|  |  | 20.465 |
| 22.8 | 22.9 |  |
|  |  | 25.013 |
|  | 34.9 |  |
| 35.2 |  |  |
|  |  | 37.390 |
| 39.7 |  |  |
|  | 40.2 |  |
|  |  | 42.312 |
| 46.5 |  |  |
|  | 47.0 |  |
|  |  | 48.836 |
| 49.5 | 49.5 |  |
|  | 50.1 |  |
| 52.3 |  |  |
|  |  | 52.431 |
|  | 52.6 |  |
|  |  | 54.443 |
| 55.9 | 55.9 |  |
|  | 56.8 |  |
|  |  | 57.792 |
| 59.2 |  |  |
|  | 59.4 |  |
|  |  | 61.240 |
| 62.6 |  |  |

TABLE 4-continued

| Form I | Form II | Form III |
|---|---|---|
|  | 64.1 |  |
|  |  | 65261 |
| 65.8 |  |  |
|  | 66.8 |  |
|  |  | 29.240 |
|  | 105.0 |  |
| 105.4 |  |  |
|  | 107.1 | 107.100 |
| 108.1 |  |  |
|  |  | 109.157 |
|  |  | 110.303 |
|  | 116.3 |  |
| 116.9 |  |  |
| 117.5 | 117.4 |  |
|  |  | 117.687 |
|  |  | 120.043 |
| 134.7 |  |  |
|  | 135.2 |  |
| 136.0 | 136.1 |  |
| 137.3 | 137.4 | 137.395 |
|  |  | 139.383 |
| 140.1 |  |  |
|  | 140.8 |  |
|  |  | 142.188 |
| 142.6 |  |  |
|  | 143.5 |  |
|  |  | 145.897 |
|  | 149.3 |  |
| 150.1 |  |  |
|  | 150.9 |  |
| 152.6 |  |  |
|  |  | 153.516 |
| 165.3 |  |  |
| 166.0 |  | 166.597 |
|  | 168.1 | 167.918 |
|  |  | 171.145 |
| 175.5 | 175.5 |  |
|  |  | 177.275 |

In the IR spectrum, the peak locations of several distinctive peaks may help one of skill in the art to identify the crystalline form of the present invention. These peaks include absorption bands at about 1159 cm$^{-1}$, 1459 cm$^{-1}$, about 1515 cm$^{-1}$, about 1623cm$^{-and}$ 2706 cm$^{-1}$. The $^{13}$C solid state NMR spectrum was measured with a Bruker MSL 300, and the IR spectrum was measured by KBr-transmission method with Perkin Elmer IR spectroscopy.

Figure 5:
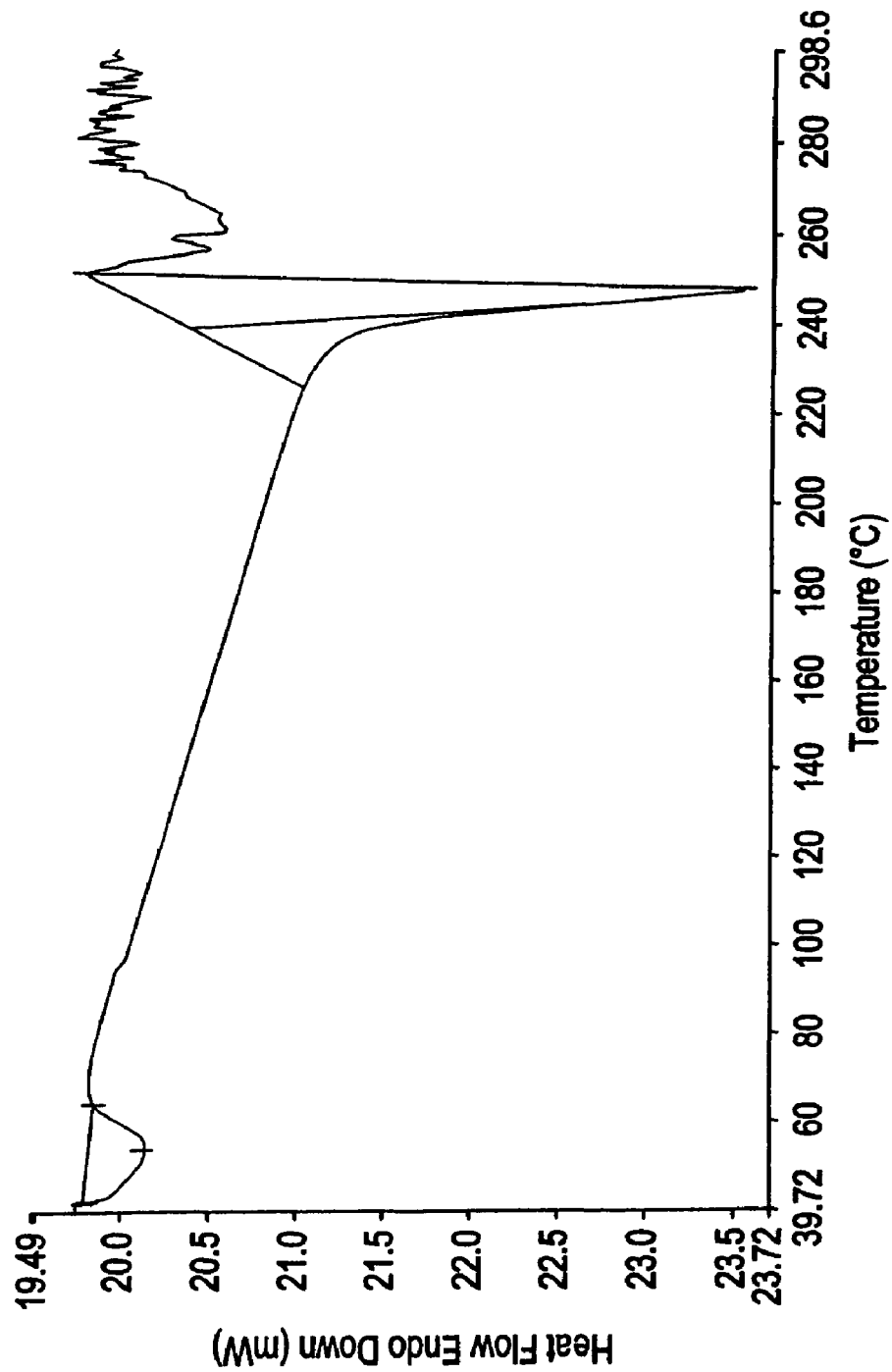
FIG. 5 is a sample of a differential scanning calorimetry thermogram of the crystalline form III of moxifloxacin monohydrochloride.

The Differential scanning calorimetry (DSC) thermogram of crystalline form of Moxifloxacin monohydrochloride obtained by the inventors is shown in FIG. 5. It exhibits a significant endo-exo pattern with identified peaks around 246° C. The DSC spectrum was measured on a Perkin Elmer Pyris 6 DSC. It is known to one of skill in the art that the endothermic peak location may be affected by the heating rate in the DSC. Thus, slight variation of the peak may be acceptable.

The invention also relates to a composition containing solid moxifloxacin monohydrochloride of which at least 80%, by total weight of the solid moxifloxacin monohydrochloride in the composition, is the crystalline form III. In the more preferred form of this composition, the solid moxifloxacin monohydrochloride is suitable for use as active ingredient in formulating pharmaceutical products. In an embodiment of the invention, the composition may comprise at least 90% of the crystalline form III of moxifloxacin monohydrochloride with respect to total weight of the solid moxifloxacin monohydrochloride in the composition. In another embodiment of the invention, the composition may comprise at least 95% of the crystalline form III of moxifloxacin monohydrochloride with respect to total weight of the solid moxifloxacin monohydrochloride in the composition. In yet another embodiment of the invention, the composition is substantially free of the form I and II of moxifloxacin monohydrochloride.

X-ray diffraction provides a convenient and practical means for quantitative determination of the relative amounts of crystalline and/or amorphous forms in a solid mixture. X-ray diffraction is adaptable to quantitative applications because the intensities of the diffraction peaks, particularly long range peaks of a given compound in a mixture are proportional to the fraction of the corresponding powder in the mixture. The percent composition of crystalline moxifloxacin monohydrochloride in an unknown composition can be determined. Preferably, the measurements are made on solid powder moxifloxacin monohydrochloride. The X-ray powder diffraction patterns of an unknown composition can be compared to known quantitative standards containing the pure crystalline form III of moxifloxacin monohydrochloride to identify the percent ratio of a particular crystalline form. This is done by comparing the relative intensities of the peaks from the diffraction pattern of the unknown solid powder composition with a calibration curve derived from the X-ray diffraction patterns of pure known samples. The curve can be calibrated based on the X-ray powder diffraction pattern for the strongest peak or any distinctive peak from a pure sample of the crystalline form III of moxifloxacin monohydrochloride. The calibration curve may be created in a manner known to those of skill in the art. For example, five or more artificial mixtures of crystalline forms of moxifloxacin monohydrochloride, at different amounts, may be prepared. In a non-limiting example, such mixtures may contain, 2%, 5%, 7%, 8%, and 10% of the crystalline III moxifloxacin monohydrochloride. Then, X-ray diffraction patterns are obtained for each artificial mixture using standard X-ray diffraction techniques. Slight variations in peak positions, if any, may be accounted for by adjusting the location of the peak to be measured. The intensities of the selected characteristic peak(s) for each of the artificial mixtures are then plotted against the known weight percentages of the crystalline form. The resulting plot is a calibration curve that allows determination of the amount of the crystalline form III of moxifloxacin monohydrochloride in an unknown sample. For the unknown mixture of the crystalline and amorphous forms of moxifloxacin monohydrochloride, the intensities of the selected characteristic peak(s) in the mixture, relative to an intensity of this peak in a calibration mixture, may be used to determine the percentage of the given crystalline form in the composition, with the remainder determined to be the amorphous material.

Similar quantitative analysis may be done using IR spectroscopy, particularly with attenuating total reflectance (ATR) technology.

Pharmaceutical compositions comprising crystalline form III of moxifloxacin monohydrochloride can be formulated with one or more pharmaceutically acceptable carriers, also known as excipients, which ordinarily lack pharmaceutical activity, but have various useful properties which may, for example, enhance the stability, sterility, bioavailability, and ease of formulation of a pharmaceutical composition. These carriers are pharmaceutically acceptable, meaning that they are not harmful to humans or animals when taken appropriately and are compatible with the other ingredients in a given formulation. The carriers may be solid, semi-solid, or liquid, and may be formulated with the compound in bulk. The resulting mixture may be manufactured in the form of a unit-dose formulation (i.e., a physically discrete unit containing a specific amount of active ingredient) such as a tablet or capsule.

Generally, the pharmaceutical compositions of the invention may be prepared by uniformly admixing the active ingredient with liquid or solid carriers and then shaping the product into the desired form. The pharmaceutical compositions may be in the form of suspensions, solutions, elixirs, aerosols, or solid dosage forms. Because of their ease of administration, tablets and capsules represent the most advantageous oral dosage unit form, in which case solid pharmaceutical carriers are employed.

A preferred oral solid preparation is a tablet. A tablet may be prepared by direct compression, wet granulation, or molding, of the active ingredient(s) with a carrier and other excipients in a manner known to those skilled in the art. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made on a suitable machine. A mixture of the powdered compound moistened with an inert liquid diluent is suitable in the case of oral solid dosage forms (e.g., powders, capsules, and tablets). If desired, tablets may be coated by standard techniques. The compounds of this invention may be formulated into typical disintegrating tablets, or into controlled or extended release dosage forms.

The pharmaceutical compositions of the invention are contemplated in various formulations suitable for various modes of administration, including but not limited to inhalation, oral, rectal, parenteral (including subcutaneous, intradermal, intramuscular, intravenous), implantable, intravaginal and transdermal administration. The most suitable route of administration in any given case depends on the duration of the subject's condition, the length of treatment desired, the nature and severity of the condition being treated, and the particular formulation that is being used. The formulations may be in bulk or in unit dosage form.

The amount of active ingredient included in a unit dosage form depends on the type of formulation that is formulated. A pharmaceutical composition of the invention will generally comprise about 0.1% by weight to about 99% by weight of active ingredient, preferably about 1% by weight to 50% by weight for oral administration and about 0.2% by weight to about 20% by weight for parenteral administration.

Formulations suitable for oral administration include capsules (hard and soft), cachets, lozenges, syrups, suppositories, and tablets, each containing a pre-determined amount of the active compound; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the active compound and a suitable carrier or carriers. For liquid oral formulations, a preferable amount is from about 2% by weight to about 20% by weight. Suitable carriers include but are not limited to fillers, binders, lubricants, inert diluents, surface active/dispersing agents, flavorants, antioxidants, bulking and granulating agents, adsorbants, preservatives, emulsifiers, suspending and wetting agents, glidants, disintegrants, buffers and pH-adjusting agents, and colorants. Examples of carriers include celluloses, modified celluloses, cyclodextrins, starches, oils, polyols, sugar alcohols and sugars, and others. For liquid formulations sugar, sugar alcohols, ethanol, water, glycerol, and polyalkylene glycols are particularly suitable, and may also be used in solid formulations. Cyclodextrins may be particularly useful for increasing bioavailability. Formulations for oral administration may optionally include enteric coatings known in the art to prevent degradation of the formulation in the stomach and provide release of the drug in the small intestine.

Formulations suitable for buccal or sub-lingual administration include lozenges comprising the active compound in a flavored base, usually sucrose and acacia or tragacanth, although other agents are also suitable, and pastilles comprising the compound in an inert base such as gelatin and glycerin or sucrose and acacia.

Formulations suitable for rectal administration are preferably presented as unit dose suppositories. These may be prepared by admixing the active compound with one or more conventional solid carriers, e.g., cocoa butter, and then shaping the resulting mixture.

In another aspect, the invention also provides methods of treating infections caused by susceptible strains of *streptococcus pneumoniae, haemophilus influenzae, moraxella catarrhalis, haemophilus parainfluenzae, klebsiella pneumoniae, staphylococcus aureus, mycoplasma pneumoniae, Chlamydia pneumoniae* and *streptococcus pyogenes*, which includes administering a mammal in need thereof an effective amount of the crystalline form III of moxifloxacin monohydrochloride.

The effective amount (i.e., dosage) of active compound for treatment will vary depending on the route of administration, the condition being treated, its severity, and duration, and the state and age of the subject. A skilled physician will monitor the progress of the subject and will adjust the dosage accordingly, depending on whether the goal is to eliminate, alleviate, or prevent a given condition. Generally, the dosage should be considered in proportion to the subject's weight. The daily dose of particular formulations of active compound may be divided among one or several unit dose administrations. For example therapeutic administration about fifteen to thirty minutes before main meals is preferable (i.e. three times daily), although administration of the active compounds may be carried out prophylactically, and may be maintained for prolonged periods of time. One skilled in the art will take such factors into account when determining dosage. Unit dosage of active ingredient may range preferably from about 1 mg to about 800 mg, more preferably from about 100 mg to about 600 mg, even more preferably from about 300 mg to about 500 mg.

The invention is further described by reference to the following examples which set forth in detail the preparation of compounds and compositions of the present invention, as well as their utility. It will be apparent to those skilled in the art, that many modifications, both to materials, and methods, may be practiced without departing from the purpose and interest of this invention. The examples that follow are not intended to limit the scope of the invention as described hereinabove or as claimed below.

REFERENCE EXAMPLE

Preparation of Moxifloxacin 1-cyclopropyl-6,7-difluoro-1,4-dihydro-4-oxo-8-methoxy quinolone-3-carboxylic acid (100 grams), (S,S) Diazabicyclo nonane (60 grams) and 1,8-Diazabicyclo[5.4.0.] undec-7-ene(DBU) (10.gms) were added to N-Methylpyrolidinone (250 ml) and the reaction mixture was slowly heated to the 60–70° C. temperature and stirred till the reaction was substantially completed. 5% aqueous isopropyl alcohol was added to the reaction mass, and pH was adjusted towards basic with caustic lye. Then the reaction mass was filtered, through clarifying filter, washed with 5% aqueous isopropyl alcohol. Combined total filtrate and adjusted pH to 7.0 to 7.2 with aqueous Hcl. and isolated at a temperature of 10–15° C. to afford moxifloxacin. Moxifloxacin then treated with Hydrochloric acid in 10% aqueous methanol to yield corresponding hydrochloride salt. (Wet weight: 115 grams)

Example 1

Preparation of Novel Crystalline Form III of Moxifloxacin Hydrochloride

Moxifloxacin hydrochloride (50 grams) (obtained from reference example) was suspended in tertiary butyl acetate (250 ml) and heated to reflux temperature of 90–100° C. Water was azeotropically removed, accompanied by cooling the reaction mixture to a temperature of 10–15° C. under stirring for 30–60 mints to crystallize the solid mass. The crystallized mass was filtered, and washed with tertiary butyl acetate (50 ml) and dried at a temperature of 60–70° C. to afford the novel crystalline form III of moxifloxacin hydrochloride. (Weight: 46.8 grams, M.C. by KF is 0.20%)

Example 2

Preparation of Novel Crystalline Form III of Anhydrous Moxifloxacin Hydrochloride Moxifloxacin Hydrochloride (115 grams) (obtained as per reference example) was dissolved in methanol (1000 ml) at reflux temperature accompanied by gently stirring for 30 min. Acetonitrile (1500 ml) was added to the above solution, the resultant solution was cooled to a temperature of 25–35° C. and stirred for 21 hrs. The obtained solid mass was filtered and dried at a temperature of 50–70° C. to afford the Novel crystalline form III of anhydrous Moxifloxacin hydrochloride.

(Weight: 49 grams, M.C. by KF is 0.2%)

Example 3

Preparation of Novel Crystalline Form III of Anhydrous Moxifloxacin Hydrochloride Moxifloxacin Hydrochloride (40 grams) (obtained from reference example) was suspended in methyl isobutyl ketone (400 ml) and heated to 110–120° C., while collecting the low boilers and refluxed azeotropically between 115–120° C. and then reaction mass is cooled to 25–35° C. and product is filtered and dried at 80–90° C. under vacuum to afford the novel crystalline form III of anhydrous Moxifloxacin hydrochloride.

(Weight: 35.8 gms, M.C. by KF is 0.20%; Purity by HPLC: 99.88%).

Example 4

Preparation of Novel Crystalline Form III of Anhydrous Moxifloxacin Hydrochloride 1-cyclopropyl-6,7-difluoro-1,4-dihydro-4-oxo-8-methoxy quinolone-3-carboxylic acid (50 Kgs), (S,S) diazabicyclo nonane (1.49 equivalents) and 1,8-diazabicyclo [5.4.0.] undec-7-ene(DBU) (5 Kgs) were added to N-methylpyrolidinone (125L) in SS Reactor and the reaction mixture was slowly heated to the 60–65° C. temperature and stirred till the reaction was substantially completed. 500L of 5% aqueous isopropyl alcohol was added to the reaction mass, and pH was adjusted to 5.0–6.0 and the product is isolated at 20–25° C. Wet cake is recrystallised in aqueous methanol at pH1.5–2.0, and is made slurry in 5% aqueous methanol. Then wet cake was dissolved in aqueous methanol and the reaction mass was filtered through clarifying filter, washed with aqueous methanol. Combined total filtrate pH was adjusted to 1.5–2.0 with Aqueous Hcl. Finally, wet cake is taken with methyl isobutylketone (800 ml) and heated to reflux while collecting the low boilers and refluxed azeotropically between 115–120° C. and then reaction mass is cooled to 25–35° C. and product is filtered and dried at 80–90° C. under vacuum to afford the novel crystalline form III of anhydrous moxifloxacin hydrochloride.

(Weight: 31.3 Kgs, M.C. by KF is 0.60%; Purity by HPLC: 99.94%).

Example 5

Soluble Granules Containing the Crystalline from III of Moxifloxacin Monohydrochloride Soluble granules containing crystalline moxifloxacin monohydrochloride may have the following content:

| Ingredient | Content (mg) |
| --- | --- |
| Crystalline Form III of anhydrous moxifloxacin monohydrochloride | 400 |
| Calcium carbonate | 800 |
| Citric acid | 900 |
| Avicel | 40 |
| Mannitol | 625 |
| Maltodextrin | 15 |
| Aspartame | 3 |
| Aroma | 20 |

Example 6

Dispersible Tablet Containing Crystalline Moxifloxacin Monohydrochloride

Dispersible tablet containing crystalline moxifloxacin monohydrochloride may have the following content:

| Ingredient | Content (mg) |
| --- | --- |
| Crystalline Form III of anhydrous moxifloxacin monohydrochloride | 400 |
| Calcium carbonate | 500 |
| Polyvinylpyrrolidone | 17 |
| Avicel | 15 |
| Mannitol | 400 |
| Maltodextrin | 15 |
| Aspartame | 3 |
| Aroma | 20 |

Example 7

A tablet Containing Anhydrous Monofloxacin Hydrochloride

A tablet containing crystalline moxifloxacin monohydrochloride had the following content:

| Ingredient | Ouantity/tab(mg) |
| --- | --- |
| Slug composition | |
| Drug Premix | |
| Moxifloxacin HCl (Anhydrous) | 436.30 |
| Colloidal Silicon Dioxide | 7.05 |
| Talc | 4.70 |
| Magnesium Stearate | 150 |
| EXCIPIENTS | 95.03 |
| Microcrystalline Cellulose (Avicel PH 112) | 140.85 |
| Lactose Monohydrate (Pharmatose DCL - 21) | 26.00 |
| Croscarmellose Sodium | 24.00 |
| Talc | 2.35 |
| Magnesium Stearate | 3.50 |
| Colloidal Silicon Dioxide | 1.75 |
| | 650.00 |
| lubrication of milled & sieved slugs | |
| Croscarmellose Sodium | 40.00 |
| Microcrystalline Cellulose (Avicel PH 112) | 24.00 |
| Talc | 6.00 |
| Magnesium Stearate | 3.50 |
| Colloidal Silicon Dioxide | 6.50 |
| Tablet Wt. | 730 |
| Film Coating (3% w/w) | |
| Opadry Beige YS-1-17174-A | 21.90 |
| Isopropyl Alcohol (70%) | q.s |
| Methylene Chloride (30%) | q.s |
| Tablet weight | 752.00 |

Unless stated to the contrary, any use of the words such as "including," "containing," "comprising," "having" and the like, means "including without limitation" and shall not be construed to limit any general statement that it follows to the specific or similar items or matters immediately following it. Except where the context indicates to the contrary, all exemplary values are intended to be fictitious, unrelated to actual entities and are used for purposes of illustration only. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

We claim:

1. A compound which is a crystalline Form III of anhydrous moxifloxacin monohydrochloride having substantially the same X-ray diffraction pattern as shown in FIG. 1.

2. The compound of claim 1 having a $^{13}$C solid state NMR spectrum comprising a peak at about 107 ppm.

3. The compound of claim 1 having substantially the same $^{13}$C solid-state NMR spectrum as shown in FIG. 2.

4. The compound of claim 1 having an infrared absorption spectrum comprising absorption bands at about 1159 cm$^{-1}$ and 2706 cm$^{-1}$.

5. The compound of claim 1 having substantially the same infrared spectrum as shown in FIG. 3.

6. The compound of claim 1 having a differential scanning calorimetry thermogram, which exhibits an endotherm peak at about 246° C.

7. The compound of claim 1 having substantially the same differential scanning calorimetry thermogram as shown in FIG. 5.

8. The compound of claim 1 having substantially the same analytical characterization data as shown in FIGS. 2, 3, 4, and 5.

9. A composition comprising moxifloxacin monohydrochloride as a solid, wherein at least 80% by weight of said solid moxifloxacin monohydrochloride is the crystalline form III of anhydrous moxifloxacin monohydrochloride of claim 1.

10. The composition of claim 9, wherein at least 90% by weight of said solid moxifloxacin monohydrochloride is in said crystalline Form III.

11. The composition of claim 9, wherein at least 95% by weight of said solid moxifloxacin monohydrochloride is in said crystalline Form III.

12. The composition of claim 9, wherein at least 99% by weight of said solid moxifloxacin monohydrochloride is in said crystalline Form III.

13. A pharmaceutical composition, which comprises a pharmaceutically effective amount of the crystalline Form III of anhydrous moxifloxacin monohydrochloride of claim 1 and one or more pharmaceutically acceptable carriers or diluents.

14. The pharmaceutical composition of claim 13, which is a solid dosage form for an oral administration.

15. The pharmaceutical composition of claim 13, wherein said solid dosage form is a tablet.

16. The pharmaceutical composition of claim 13, which is in dosage unit form containing from about 0.5 to about 800 mg of moxifloxacin monohydrochloride.

17. A process for preparation of the crystalline Form III of moxifloxacin monohydrochloride of claim 1, said process comprising: a) refluxing azeotropically a starting moxifloxacin monohydrochloride in a solvent selected from the group consisting of lower branched esters, chained acid esters, aliphatic ketones and aliphatic hydrocarbon solvents; b) cooling the refluxed solvent while stirring the mixture until a solid separates; and c) isolating said separated solid thereby obtaining said crystalline Form III of anhydrous moxifloxacin monohydrochloride.

18. The process of claim 17, wherein said solvent is selected from the group consisting of tertiary butyl acetate, cyclohexane, toluene, methylisobutylketone, and mixtures thereof.

19. A process for preparation of the crystalline Form III of moxifloxacin monohydrochloride of claim 1, said process comprising: a) dissolving moxifloxacin hydrochloride in a lower alkyl alcohol to obtain a solution; b) adding to the solution an anti solvent, in which moxifloxacin hydrochloride is poorly soluble; c) cooling the mixed solvents until a solid separates; and d) isolating said solids thereby obtaining said crystalline Form III of moxifloxacin monohydrochloride.

20. The process of claim 19, wherein said lower alkyl alcohol is selected from the group consisting of methanol, ethanol, t-butyl alcohol, isopropyl alcohol and mixtures thereof.

21. The process of claim 19, wherein said lower alkyl alcohol is methanol.

22. The process of claim 19, wherein said anti solvent is acetonitrile.

23. The moxifloxacin monohydrochloride produced in accordance with the process of claim 17.

24. The moxifloxacin monohydrochloride produced in accordance with the process of claim 19.

25. A method of treating infections caused by susceptible strains of *streptococcus pneumoniae, haemophilus influenzae, moraxella catarrhalis, haemophilus parainfluenzae, klebsiella pneumoniae, staphylococcus aureus, mycoplasma pneumoniae, Chlamydia pneumoniae* and *streptococcus pyogenes*, which comprises administering a mammal in need thereof an effective amount of the crystalline Form III of moxifloxacin monohydrochloride of claim 1.

26. The method of claim 25, wherein said mammal is a human.

* * * * *

UNITED STATES PATENT AND TRADEMARK OFFICE
CERTIFICATE OF CORRECTION

PATENT NO. : 7,230,006 B2  
APPLICATION NO. : 10/822154  
DATED : June 12, 2007  
INVENTOR(S) : Manne Satyanarayana Reddy et al.

It is certified that error appears in the above-identified patent and that said Letters Patent is hereby corrected as shown below:

Title page, item [73]

Please correct the Assignee names from:

"Reddy's Laboratories Limited" and "Reddy's Laboratories, Inc."

to:

-- Dr. Reddy's Laboratories Limited -- and -- Dr. Reddy's Laboratories, Inc. --.

Title page, item [30]

Please correct the Foreign Application Priority Data from:

"Sep. 4, 2003"

to:

-- April 9, 2003 --.

Signed and Sealed this

Seventh Day of August, 2007

JON W. DUDAS  
*Director of the United States Patent and Trademark Office*